United States Patent [19]

Nassar et al.

[11] Patent Number: 4,882,356

[45] Date of Patent: Nov. 21, 1989

[54] STABLE INJECTABLE ANTIEMETIC COMPOSITIONS

[76] Inventors: Munir N. Nassar, 5100 Highbridge St., #51F; Shreeram N. Agharkar, 7290 Wakefield Dr., both of Fayetteville, N.Y. 13066; Joseph B. Bogardus, 8239 Penstock Way, Manlius, N.Y. 13104

[21] Appl. No.: 19,733

[22] Filed: Mar. 10, 1987

[51] Int. Cl.[4] .......... A61K 31/165

[52] U.S. Cl. .......... 514/619; 514/970

[58] Field of Search .......... 514/619, 970

[56] References Cited

U.S. PATENT DOCUMENTS

| | | | |
|---|---|---|---|
| Re. 26,541 | 3/1969 | Remmers et al. | 514/970 |
| 4,323,577 | 4/1982 | Ohkuma et al. | 514/970 |

FOREIGN PATENT DOCUMENTS 2160871 1/1986 United Kingdom .

OTHER PUBLICATIONS

Remington's Pharmaceutical Sciences, 15th Ed. (1975), Mack Pub. Co., Easton, PA, p. 1465.

*PDR,* 42 Ed. (1988), pp. 1696–1698.

*Remington's Pharmaceutical Sciences,* 15th Ed. (1975), Mack Publishing Company, Easton, PA, pp. 165 & 166.

*Primary Examiner*—Frederick E. Waddell

[57] ABSTRACT

Stable, injectable, aqueous solutions of 4-amino-5-chloro-N-[2-(diethylamino)ethyl]-2-[(substituted)alkoxy]benzamide antiemetic agents are prepared by adding, as stabilizing agent, a pharmaceutically acceptable, water-miscible, hydroxylic organic solvent or water-soluble polyhydric alcohol or sugar which decreases the polarity of the solution.

12 Claims, No Drawings

STABLE INJECTABLE ANTIEMETIC COMPOSITIONS

SUMMARY OF THE INVENTION

This invention relates to stable, injectable, aqueous solutions of 4-amino-5-chloro-N-[2-(diethylamino)ethyl]-2-[(substituted)alkoxy]benzamide antiemetic agents containing, as stabilizing agent, a pharmaceutically acceptable, water-miscible, hydroxylic organic solvent or water-soluble polyhydric alcohol or sugar which decreases the polarity of the solution.

BACKGROUND AND DESCRIPTION OF THE PRIOR ART

Methods for the stabilization of medicaments vary widely, depending on the type of medicament. The addition of a reducing agent to an easily oxidized medicament is a well-known example. Ascorbic acid has been stabilized against oxidation by the use of a mixed solvent having a decreased dissolved oxygen content. The degradation (by hydrolysis) of some anesthetic esters has been inhibited by the addition of caffeine, which was shown to complex with the esters. The series of "paraben" preservatives, e.g., methyl paraben, ethyl paraben, propyl paraben and butyl paraben, are well-known stabilizers used in numerous pharmaceutical compositions. U.S. Pat. No. 4,328,213, issued on May 4, 1982 to V. Ecker et al., for example, describes and claims their use in the stabilization of injectable labetalol formulations.

The antiemetic agents utilized in the stable formulations described and claimed herein are known compounds, having been described, for example, in published U.K. Patent Application 2,160,871 A, published Jan. 2, 1986, the disclosure of which is incorporated herein by reference.

Metoclopramide is a well-known antiemetic agent with a structure similar to the antiemetic agents utilized herein, except that it contains a methoxy group in the 2-position. The Physicians' Desk Reference, 36th edition, 1982, pages 1565-6, shows that the injectable form of metoclopramide sold at that time was stabilized with sodium metabisulfite.

Published U.K. Patent Application 2,158,714 A, published Nov. 20, 1985, confirms that injectable metoclopramide formulations were then stabilized with sodium metabisulfite. It goes on to point out that metoclopramide was being used in conjunction with cisplatinum chemotherapy for cancer, and that cisplatinum had been found to be incompatible with sodium metabisulfite. It states that it was found that, surprisingly, sodium metabisulfite could be eliminated from injectable metoclopramide formulations without unduly affecting their stability.

In *Chem. Pharm. Bull.*, 8, 504 (1960), K. Ikeda reports the results of a study which showed increased stability of certain barbiturates in water-ethanol or water-methanol solutions having reduced dielectric constants, as compared with aqueous solutions of the barbiturates.

In *Chem. Pharm. Bull.*, 8, (1960), K. Ikeda reports that the same barbiturates have increased stability in aqueous solutions of ethylene glycol, propylene glycol, glycerol, glucose, mannitol and sucrose. However, his studies showed that the stabilization could not be attributed only to the change of dielectric constant of the medium. Moreover, he refers to the work of E. S. Amis et al. in *J. Am. Chem. Soc.*, 63, 2621 (1940) with the alkaline degradation of bromthymol blue. Amis et al. found that the reaction between negative bivalent dye ion and hydroxyl ion was in accordance with the theory in methanol-water and ethanol-water, but in glycerol-water mixture the activation energy was opposite to the theory on dielectric constant.

In *J. Am. Pharm. Assoc.*, 48, 77 (1959), A.D. Marcus et al. refer to "the widespread use of mixed solvents in pharmaceuticals and the relative lack of information concerning the effects of such solvent systems upon the stability of the active ingredients". They point out that any assumption that replacement of part of the water by a non-aqueous solvent is some sort of a panacea is erroneous, and probably results from a lack of appreciation of the ability of non-aqueous solvents, especially those which are hydroxylic, to participate in, or otherwise influence, solvolytic reactions. In a study of the hydrogen ion catalyzed solvolysis of chloramphenicol in water-propylene glycol solutions, they found that the addition of propylene glycol to the aqueous solution increased the rate of solvolysis of the chloramphenicol.

COMPLETE DISCLOSURE

This invention relates to stable, injectable, aqueous solutions of antiemetic agents having the Formula I

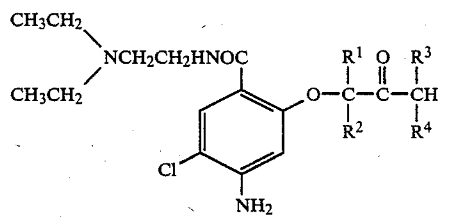

I wherein $R^1$, $R^2$ and $R^3$ each are independently hydrogen or methyl, and $R^4$ is hydrogen, a straight or branched chain alkyl group containing from 1 to 4 carbon atoms or, when $R^3$ is hydrogen, $R^4$ may be phenyl, or a nontoxic, pharmaceutically acceptable acid addition salt thereof, containing as stabilizing agent a pharmaceutically acceptable, water-miscible, hydroxylic organic solvent or water-soluble polyhydric alcohol or sugar which decreases the polarity (dielectric constant) of the solution. Preferred organic hydroxylic stabilizers include ethanol, propylene glycol glycerol and mannitol, with glycerol being the most preferred. A particularly preferred pharmaceutically acceptable acid addition salt of a compound of Formula I is the hydrochloride. The most preferred compound of Formula I is the compound wherein $R^1$, $R^3$ and $R^4$ are hydrogen, and $R^2$ is methyl, which is named 4-amino-2-(2-butanon-3-yl)oxy-5-chloro-N-[2-(diethylamino)ethyl]benzamide (Ia).

The compounds of Formula I in aqueous, isotonic (isotonicity adjusted with sodium chloride and/or dextrose) and buffered (0.1M citrate and phosphate buffers, pH 5.7 and 6.5) formulations containing the equivalent of 5 mg of free base of a compound of Formula I per ml have been found unsuitable for long term shelf life. Typical isotonic and buffered formulations lost 33% and 40%, respectively, of their potency following storage for eight weeks at 56° C. The compound of Formula Ia, for example, has been found to degrade via an intramolecular cyclization reaction leading to the formation of the compound of Formula II

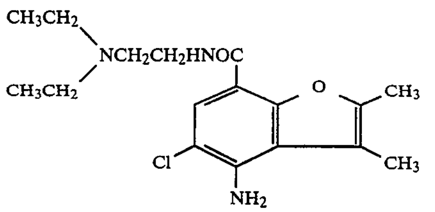

II which was isolated and identified. Tables 1 and 2 give the results of stability tests on the compound of Formula Ia in water and in isotonic saline, and in citrate buffers, respectively.

TABLE 1

Stability of Compound Ia (5 mg/ml) in Water and Isotonic Saline at 56° C.

| Time (Weeks) | % Remaining (a) (Water) | % Remaining (a) (Isotonic Saline) |
|---|---|---|
| Initial | 100.0 | 100.0 |
| 1 | 97.4 | 96.0 |
| 2 | 95.5 | 91.6 |
| 4 | 90.8 | 83.5 |
| 8 | 80.5 | 66.9 |

(a) Reported values are the average of duplicate samples.

TABLE 2

Stability of Compound Ia (5 mg/ml) in 0.01 M Citrate Buffers at pH 5.7 and 6.5 at 56° C.

| Time (Weeks) | % Remaining (a) (pH 5.7) | % Remaining (a) (pH 6.5) |
|---|---|---|
| Initial | 100.0 | 100.0 |
| 1 | 94.8 | 93.6 |
| 2 | 87.8 | 87.9 |
| 4 | 77.2 | 77.5 |
| 8 | 58.9 | 60.3 |

(a) Reported values are the average of duplicate samples.

According to the present invention it has been found that a stable, injectable, aqueous formulation of a compound of Formula I can be attained by the addition of a pharmaceutically acceptable hydroxylic organic solvent or water soluble polyhydric alcohol or sugar to lower the dielectric constant (polarity) of the solution. Preferred hydroxylic stabilizers include ethanol, propylene glycol, glycerol and mannitol with glycerol being the most preferred.

The amount of hydroxylic stabilizer to be added may vary from about 5% up to about 75% depending on the actual compound used. However, we prefer to use from about 5% to about 30%, and most preferably from about 10% to about 20%. For example, we have found that compositions containing 75% ethanol are among the most stable but, because of potential undesirable side effects from the intravenous administration of moderate amounts of ethanol, we prefer to use much lower amounts of ethanol or even to use a different hydroxylic solvent such as glycerol. Even glycerol, in high dosage may cause undesirable side effects and, for that reason, we most prefer to use the stabilizer at a concentration of about 10%.

The amount of Compound I per ml of stable formulation may vary from 1 mg to about 50 mg or even more, depending on the particular compound. We prefer to use at least 1 mg/ml and up to about 40 mg/ml.

The pH of the final composition should be in the range of from about 4 to about 7, and preferably is from about 5.0 to about 6.7. Most preferably, the pH is within the range of from about 6.0 to about 6.5.

Optionally, about 9 mg/ml of the preservative benzyl alcohol may be added to the formulation. This is particularly desirable if the formulation is packaged in multiple dose form.

The pharmaceutically acceptable acid addition salts of the compounds of Formula I may be derived from any of the acids commonly used in the pharmaceutical art. Preferred salts are the sulfate, maleate, tartrate, citrate and hydrochloride, with the hydrochloride being the most preferred.

The hydroxylic stabilizing compounds utilized herein, such as ethanol, propylene glycol, glycerol and mannitol, all lower the dielectric constant of the formulations. Although we believe that the stabilizing effect is due, at least partially, to the lowered dielectric constant of the formulations, we do not intend to limit ourselves to any particular theory.

The dosage of the compounds of Formula I depend on the particular active ingredient, the age, weight and general health of the patient, as well as the severity of the malady, and is within the discretion of the physician. For the prevention of nausea and vomiting associated with emetogenic cancer chemotherapeutic agents, the compounds of Formula I are generally administered at a dosage of from about 1 mg/kg to about 50 mg/kg, given several times per day.

EXAMPLE 1

| Ingredient | Amount/ml |
|---|---|
| Compound Ia Hydrochloride | 5.51 mg |
| Glycerol | 200 mg |
| Sodium Hydroxide (0.01 N) | 65 μl |
| Water for Injection q.s. ad | 1.00 ml |

Procedure for Formulation

Into a suitable compounding vessel add an excess of the batch volume of Water for Injection. Heat to boiling and allow the water to boil for ten minutes. While cooling, cover the container, bubble nitrogen through the water and keep a jet of nitrogen on top. Withdraw part of the water, leaving approximately 70% of the batch volume of water in the compounding vessel. Quantitatively add the glycerol with continuous stirring until complete mixing is achieved. Add the active ingredient and the sodium hydroxide solution. Bring the solution to final volume, filter it through a sterilizing membrane and fill into sterile containers with a nitrogen overlay.

EXAMPLE 2

| Ingredient | Amount/ml |
|---|---|
| Compound Ia Hydrochloride | 5.51 mg |
| Propylene Glycol | 200 mg |
| Sodium Hydroxide (0.01 N) | 70 μl |
| Water for Injection q.s. ad | 1.00 ml |

Procedure for Formulation

Into a suitable compounding vessel add an excess of the batch volume of Water for Injection. Heat to boiling and allow the water to boil for ten minutes. While cooling, cover the container, bubble nitrogen through the water and keep a jet of nitrogen on top. Withdraw part of the water, leaving approximately 70% of the batch volume of water in the compounding vessel. Quantitatively add the propylene glycol with continuous stirring until complete mixing is achieved. Add the active ingredient and the sodium hydroxide solution. Bring the solution to final volume, filter it through a sterilizing membrane and fill into sterile containers with a nitrogen overlay.

EXAMPLE 3

| Ingredient | Amount/ml |
|---|---|
| Compound Ia Hydrochloride | 5.51 mg |
| Ethyl Alcohol | 200 mg |
| Sodium Hydroxide (0.01 N) | 55 μl |
| Water for injection q.s. ad | 1.00 ml |

Procedure for Formulation

Into a suitable compounding vessel add an excess of the batch volume of Water for Injection. Heat to boiling and allow the water to boil for ten minutes. While cooling, cover the container, bubble nitrogen through the water and keep a jet of nitrogen on top. Withdraw part of the water, leaving approximately 70% of the batch volume of water in the compounding vessel. Quantitatively add the ethyl alcohol with continuous stirring until complete mixing is achieved. Add the active ingredient and the sodium hydroxide solution. Bring the solution to final volume, filter it through a sterilizing membrane and fill into sterile containers with a nitrogen overlay.

EXAMPLE 4

| Ingredient | Amount/ml |
|---|---|
| Compound Ia Hydrochloride | 44.1 mg |
| Glycerol | 200 mg |
| Sodium Hydroxide (0.01 N) | to pH 6.0-6.2 |
| Water for Injection q.s. ad | 1.00 ml |

Procedure for Formulation

Into a suitable compounding vessel add an excess of the batch volume of Water for Injection. Heat to boiling and allow the water to boil for ten minutes. While cooling, cover the container, bubble nitrogen through the water and keep a jet of nitrogen on top. Withdraw part of the water, leaving approximately 70% of the batch volume of water in the compounding vessel. Quantitatively add the glycerol with continuous stirring until complete mixing is achieved. Add the active ingredient and the sodium hydroxide solution. Bring the solution to final volume, filter it through a sterilizing membrane and fill into sterile containers with a nitrogen overlay.

EXAMPLE 5

| Ingredient | Amount/ml |
|---|---|
| Compound Ia Hydrochloride | 11.0 mg |
| Glycerol | 350 mg |
| Sodium Hydroxide (0.01 N) | to pH 6.0-6.2 |
| Water for Injection q.s. ad | 1.00 ml |

Procedure for Formulation

Into a suitable compounding vessel add an excess of the batch volume of Water for Injection. Heat to boiling and allow the water to boil for ten minutes. While cooling, cover the container, bubble nitrogen through the water and keep a jet of nitrogen on top. Withdraw part of the water, leaving approximately 70% of the batch volume of water in the compounding vessel. Quantitatively add the glycerol with continuous stirring until complete mixing is achieved. Add the active ingredient and the sodium hydroxide solution. Bring the solution to final volume, filter it through a sterilizing membrane and fill into sterile containers with a nitrogen overlay.

EXAMPLE 6

| Ingredient | Amount/ml |
|---|---|
| Compound Ia Hydrochloride | 1.1025 mg |
| Glycerol | 100.0 mg |
| Benzyl Alcohol | 9.0 mg |
| Sodium Hydroxide (1.0 N) | to pH 6.3 ± 0.2 |
| Water for Injection q.s. ad | 1.00 ml |

EXAMPLE 7

| Ingredient | Amount/ml |
|---|---|
| Compound Ia Hydrochloride | 11.025 mg |
| Glycerol | 100.0 mg |
| Benzyl Alcohol | 9.0 mg |
| Sodium Hydroxide (1.0 N) | to pH 6.3 ± 0.2 |
| Water for Injection q.s. ad | 1.00 ml |

EXAMPLE 8

| Ingredient | Amount/ml |
|---|---|
| Compound Ia Hydrochloride | 27.56 mg |
| Glycerol | 100.0 mg |
| Benzyl Alcohol | 9.0 mg. |
| Sodium Hydroxide (1.0 N) | to pH 6.3 ± 0.2 |
| Water for Injection q.s. ad | 1.00 ml |

Procedure for Formulation of Examples 6, 7 and 8

In a suitable vessel, collect 80% of the required amount of Water for Injection and overlay with nitrogen. While stirring, add and dissolve the Glycerol, Benzyl Alcohol and Compound Ia. Agitate to ensure homogeniety and continuously overlay with Nitrogen, NF. Adjust the pH of the solution to 6.3±0.2 by addition of 1N Sodium Hydroxide Solution. Bring the solution to the desired batch volume with Water for Injection, and stir to ensure complete dissolution. Aseptically filter the solution using a sterilized membrane filter, and collect the filtrate in a sterilized receiving vessel. Fill the solution into sterilized ampules, overlay with nitrogen and seal the ampules.

Tables 3 and 4, below, provide stability data for some of the stable injectable formulations of the present invention.

TABLE 3

Stability of Compound Ia (5 mg/ml) in Ethanol-Water Mixtures at 56° C.

| Ethanol/Water (v/v) | Calculated Dielectric Constant | % Remaining (4 weeks) | % Remaining (8 weeks) |
|---|---|---|---|
| 0/100 | 78.5 | 94.9 | 89.4 |
| 25/75 | 64.9 | 98.7 | 97.5 |
| 50/50 | 51.4 | 99.5 | 99.1 |

TABLE 3-continued

| Stability of Compound Ia (5 mg/ml) in Ethanol-Water Mixtures at 56° C. | | | |
|---|---|---|---|
| Ethanol/Water (v/v) | Calculated Dielectric Constant | % Remaining (4 weeks) | % Remaining (8 weeks) |
| 75/25 | 37.8 | 99.6 | 99.6 |

TABLE 4

| Stability of Compound Ia (5 mg/ml) in Propylene Glycol-Water and Glycerol-Water at 56° C. | | | |
|---|---|---|---|
| Solvent | Calculated Dielectric Constant | % Remaining (4 weeks) | % Remaining (8 weeks) |
| Water | 78.5 | 94.9 | 88.1 |
| 25% (w/v) Propylene Glycol | 67.3 | 97.7 | 96.8 |
| 5% (w/v) Glycerol | 76.3 | 95.1 | 90.9 |
| 15% (w/v) Glycerol | 71.8 | 96.5 | 94.2 |
| 25% (w/v) Glycerol | 71.4 | 96.8 | 95.3 |

We claim:

1. A method for inhibiting degradation via an intramolecular cyclization reaction of an arithmetic compound of the formula

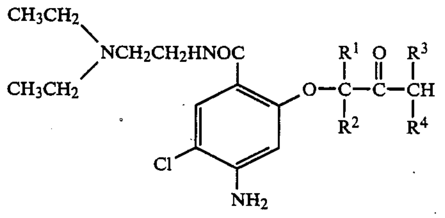

I wherein $R^1$, $R^2$ and $R^3$ each are independently hydrogen or methyl, and $R^4$ is hydrogen, a straight or branched chain alkyl group containing from 1 to 4 carbon atoms or, when $R^3$ is hydrogen, $R^4$ may be phenyl, or a non-toxic, pharmaceutically acceptable acid addition salt thereof, which comprises mixing an aqueous solution of a therapeutically effective amount from about 0.1% to about 5% (w/v) of said compound with a stabilizing agent which is a pharmaceutically acceptable water-miscible hydroxylic organic solvent in an amount of from about 5% to about 75% (w/v) or a water-soluble polyhydric alcohol in an amount of from about 5% to about 35% (w/v).

2. The method of claim 1 wherein the stabilizing agent is selected from ethanol, propylene glycol and glycerol, and is present in an amount of from about 5% to about 30% (w/v).

3. The method of claim 2 wherein the compound of Formula I is present in an amount of from about 0.1% to about 4% (w/v).

4. The method of claim 3 wherein the pH of the final solution is in the range of from about 5.0 to about 6.7.

5. The method of claim 4 wherein the compound of Formula I is 4-amino-2-(2-butanon-3-yl)oxy-5-chloro-N-[2-(diethylamino)ethyl]benzamide.

6. The method of claim 5 wherein the stabilizing agent is ethanol.

7. The method of claim 5 wherein the stabilizing agent is propylene glycol.

8. The method of claim 5 wherein the stabilizing agent is glycerol.

9. The method of claim 8 wherein the compound of Formula I is present as the hydrochloride salt and the pH of the final solution is in the range of from about 6.0 to about 6.5.

10. The method of claim 9 wherein the glycerol is present in an amount of about 10% (w/v).

11. The method of claim 4 which additionally contains benzyl alcohol as a preservative.

12. The method of claim 10 which additionally contains about 9 mg of benzyl alcohol per ml as a preservative.

* * * * *